(12) United States Patent
Ikeda

(10) Patent No.: US 6,533,936 B1
(45) Date of Patent: Mar. 18, 2003

(54) METHOD FOR SEPARATION OF OPTICAL ISOMERS

(75) Inventor: Hirokazu Ikeda, Ako (JP)

(73) Assignee: Daicel Chemical Industries, Ltd. (JP)

( * ) Notice: Subject to any disclaimer, the term of this patent is extended or adjusted under 35 U.S.C. 154(b) by 0 days.

(21) Appl. No.: 08/951,502

(22) Filed: Oct. 16, 1997

Related U.S. Application Data

(63) Continuation of application No. 08/564,321, filed as application No. PCT/JP95/00768 on Apr. 19, 1995, now abandoned.

(30) Foreign Application Priority Data

Apr. 20, 1994 (JP) .............................................. 6-81479

(51) Int. Cl.[7] .............................................. B01D 15/08
(52) U.S. Cl. ..................... 210/635; 210/656; 210/198.2
(58) Field of Search ................. 210/635, 656, 210/659, 198.2, 502.1; 435/280

(56) References Cited

U.S. PATENT DOCUMENTS

| | | | | |
|---|---|---|---|---|
| 4,861,872 A | * | 8/1989 | Okamoto | .................. 536/18.7 |
| 5,091,520 A | | 2/1992 | Francotte et al. | ............. 536/56 |
| 5,126,055 A | * | 6/1992 | Yamashita | ................... 210/659 |
| 5,354,852 A | * | 10/1994 | Ikeda | .......................... 536/17.9 |
| 5,434,298 A | * | 7/1995 | Negawa | ...................... 210/659 |
| 5,434,299 A | * | 7/1995 | Negawa | ...................... 210/659 |
| 5,456,825 A | * | 10/1995 | Negawa | ................... 210/198.2 |
| 5,498,752 A | * | 3/1996 | Negawa | ...................... 210/659 |
| 5,518,625 A | * | 5/1996 | Priegnitz | .................... 210/659 |

FOREIGN PATENT DOCUMENTS

WO     WO9215635    *   9/1992      ............. 210/198.2

OTHER PUBLICATIONS

Negawa, et al., J. Chromatography 590:113–117 (1992).*
Negamatsu, Chiral Europe '96 (1990) pp. 1–5.*

* cited by examiner

Primary Examiner—Ernest G. Therkorn
(74) Attorney, Agent, or Firm—Browdy and Neimark, PLLC

(57) ABSTRACT

The method of separation of optical isomers in accordance with the present invention is directed to providing a method of separation of optical isomers which enables efficient optical resolution of optical isomer mixture not using expensive silica gel but using a filler which is inexpensive per se and has excellent optical resolution ability, and characterized in that particles of polysaccharide derivatives, preferably ester derivatives and carbamate derivatives of polysaccharide are used as an optical resolution filler.

11 Claims, 2 Drawing Sheets

METHOD FOR SEPARATION OF OPTICAL ISOMERS

This application is a continuation of application Ser. No. 08/564,321, filed Dec. 19, 1995, now abandoned, which is a 35 USC § 371 national stage application of PCT/JP95/00768, filed Apr. 19, 1995.

FIELD OF THE INVENTION

The present invention relates to a method for separation of optical isomers. More particularly, the present invention relates to an efficient method for optical resolution of optical isomers using simulated moving bed chromatographic apparatus.

BACKGROUND OF THE INVENTION

As an industrial method for isolating an object component from an isomer mixture stock solution containing more than one isomers, chromatography is widely employed.

Chromatography is a method of separation comprising using an adsorption column packed with an adsorbent such as ion exchange resin, zeolite, silica gel and the like as a filler and separating components by making use of the difference in their adsorbabilities by the adsorbent. In this method, water, an organic solvent or a mixture thereof is used as an eluent. A high purity object component can be obtained by concentrating the eluent portion containing the object component.

There are known batch system chromatography and simulated moving bed chromatography.

Especially, simulated moving bed chromatography is very hopeful as a method for commercial scale separation of isomers for the reasons that the required amount of the eluent is smaller than required in the batch system chromatography, continuous separation of components is possible, etc.

In simulated moving bed chromatography, however, an expensive support such as silica gel must be used for the filler. The fact that there is no inexpensive effective filler provided with excellent optical resolution ability has been an obstacle to the positive employment of simulated moving bed chromatography, the apparatus for which is also relatively expensive per se.

Therefore, an adsorbent, which does not require expensive silica gel as a support, is inexpensive per se and has excellent ability of separating optically active isomers, has been desired.

This invention is made under the above-described circumstances. That is, the object of this invention is to provide a method for separation of optical isomers which is able to efficiently effect optical resolution of an optical isomer mixture using a filler for optical resolution, which is inexpensive per se, has excellent ability of optical resolution and requires no expensive silica gel support.

DISCLOSURE OF THE INVENTION

We intensively coped with the problem and found, in the separation method using the simulated moving bed chromatographic apparatus, that optical isomer mixtures can be efficiently separated by using particles of a polysaccharide derivative as a filler for optical resolution without using expensive silica gel and completed the present invention.

A first embodiment of this invention is, in the method of separation of optical isomers, which comprises using a simulated moving bed chromatographic apparatus comprised of a plurality of columns packed with an optical resolution filler and endlessly connected and a circulating pump which circulates a fluid in one direction through the plurality of the columns, wherein an optical isomer mixture solution and an eluent are introduced into said fluid flow and simultaneously a solution rich in non-adsorbable or poorly-adsorbable substances and a solution rich in adsorbable or strongly adsorbable substances are simultaneously taken out, an inlet for a fluid to be introduced into the columns and an outlet for a fluid to be taken out of the columns are alternately arranged in the direction of the circulating fluid and said inlet and outlet are intermittently shifted in the direction of the fluid flow, a method characterized in that particles of a polysaccharide derivative are used as said filler for optical resolution.

A second embodiment of the invention is a method of separation of optical isomers of the first embodiment in which an ester derivative and/or a carbamate derivative of the polysaccharide is used.

A third embodiment of this invention is a method of separation of optical isomers of the first embodiment in which the polysaccharide derivative is that in which all or a part of hydrogen atoms of the hydroxyl or amino groups of the polysaccharide are substituted with at least one of the atom groups represented by the following formula (1), (2), (3) or (4):

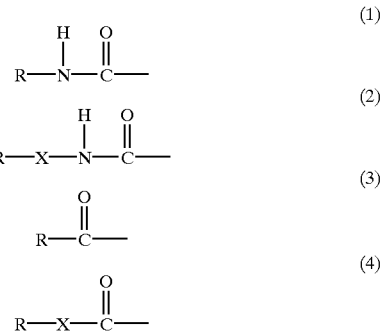

wherein R is an aromatic group which may contain a hetero atom and may be unsubstituted or substituted with at least one group or atom selected from a class consisting of $C_{1-12}$ alkyl group, $C_{1-12}$ alkoxyl group, $C_{1-12}$ alkylthio group, cyano group, halogen atom, $C_{1-8}$ acyl group, $C_{1-8}$ acyloxy group, hydroxyl group, $C_{1-12}$ alkoxycarbonyl group, nitro group, amino group and $C_{1-8}$ dialkylamino group; and X is a $C_{1-4}$ hydrocarbyl group which may contain a double bond or a triple bond.

A fourth embodiment of this invention is a method of separation of optical isomers of said first or second embodiment, in which the polysaccharide derivative is a carbamate derivative of polysaccharide which is obtained by reacting an isocyanate represented by the following formula (5) or (6) with the polysaccharide or an ester derivative of polysaccharide which is obtained by reacting an acid chloride represented by the following formula (7) or (8) with the polysaccharide:

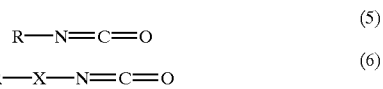

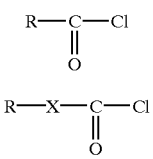

(7)

(8)

wherein R is an aromatic group which may contain a hetero atom and may be unsubstituted or substituted with at least one group or atom selected from a class consisting of $C_{1-12}$ alkyl group, $C_{1-12}$ alkoxyl group, $C_{1-12}$ alkylthio group, cyano group, halogen atom, $C_{1-8}$ acyl group, $C_{1-8}$ acyloxy group, hydroxyl group, $C_{1-12}$ alkoxycarbonyl group, nitro group, amino group and $C_{1-8}$ dialkylamino group; and X is a $C_{1-4}$ hydrocarbyl group which may contain a double bond or a triple bond.

A fifth embodiment of this invention is a method of separation of optical isomers of any of said first to fourth embodiments in which the polysaccharide is cellulose.

A sixth embodiment of this invention is a method of separation of optical isomers of any of said first to fifth embodiments, in which the number average degree of polymerization is not less than 5.

A seventh embodiment of this invention is a method of separation of optical isomers of any of said first to sixth embodiments, in which the number average degree of polymerization is 10–2,000.

An eighth embodiment of this invention is a method of separation of optical isomers of any of said first to seventh embodiments, in which the degree of introduction of the substituents in the polysaccharide is 10–100%.

A ninth embodiment of this invention is a method of separation of optical isomers of any of said first to seventh embodiments, in which the degree of introduction of the substituents in the polysaccharide is 30–100%.

A tenth embodiment of this invention is a method of separation of optical isomers of any of said first to ninth embodiments, in which said derivative of the saccharide is in the form of particles having a particle diameter of 10–300 μm, a specific surface area of 0.5–300 m²/g.

BRIEF DESCRIPTION OF THE ATTACHED DRAWINGS

BEST MODE OF WORKING OF THE PRESENT INVENTION

Figure 1:
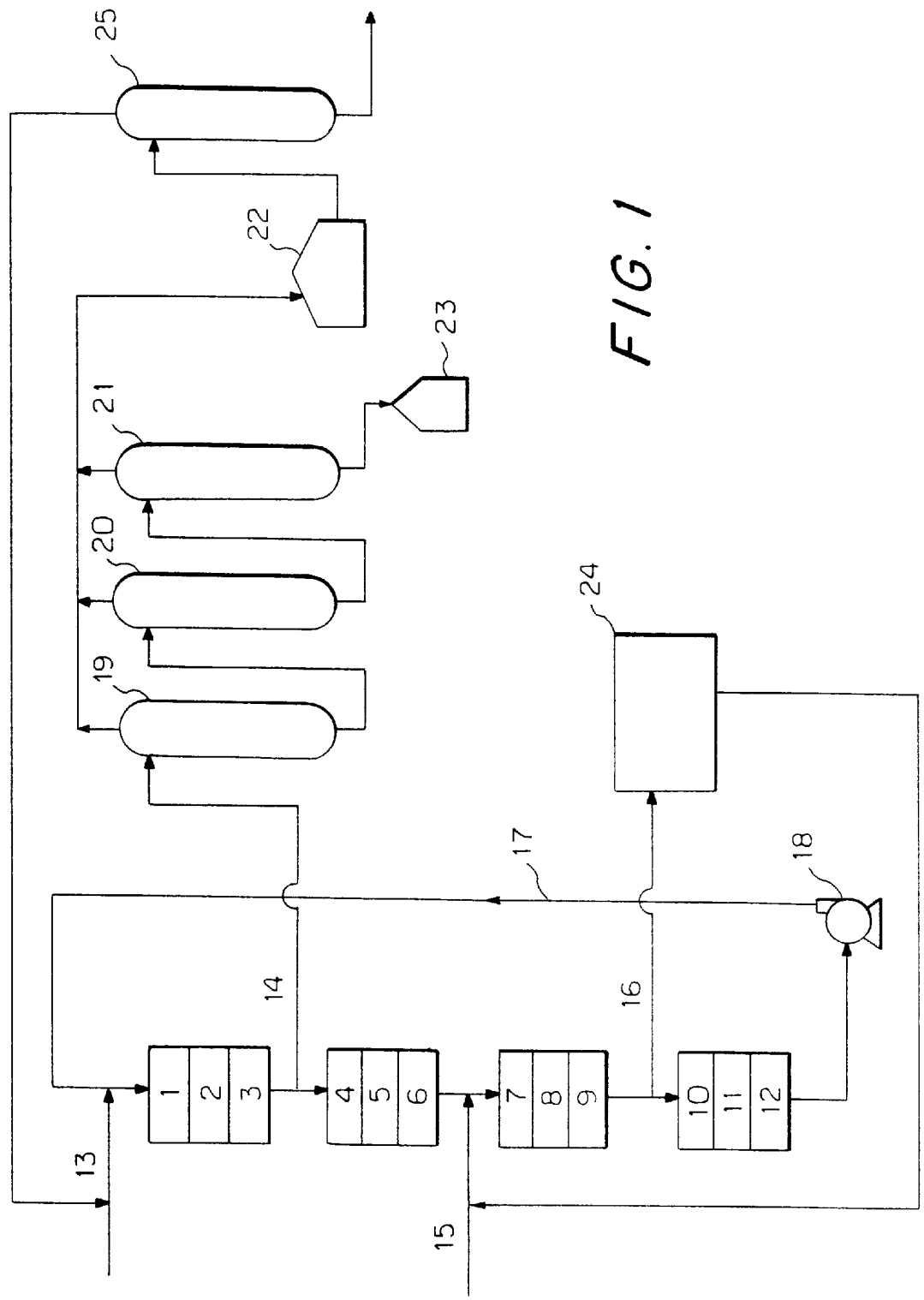
FIG. 1 is a schematic presentation showing an example of the simulated moving bed chromatographic apparatus used for the present invention.

Mixtures of optical isomers to be separated by the method of the present invention include racemic compounds or mixtures which are obtained by asymmetric synthesis and contain one optical isomer in excess.

In the present invention, particles of polysaccharide derivatives are used as fillers for optical resolution. Particles of polysaccharide derivatives are not specifically limited and particles of various polysaccharide derivatives can be used.

The polysaccharide of said polysaccharide derivatives encompasses natural polysaccharides, modified natural polysaccharides and synthetic polysaccharides and all these are applicable insofar as they are optically active.

Specific examples of the polysaccharide of polysaccharide derivatives are: α-1,4-glucan (amylose, amylopectin), β-1,4-glucan (cellulose), α-1,6-glucan (dextran), β1,6-glucan (pustulan), β-1,3-glucan (curdlan, schizophyllan), α-1,3-glucan, β-1,2-glucan (Crawn Gall polysaccharide), β-1,4-galactan, α-1,6-mannan, β-1,4-mannan, β-1,2-fructan (inuline), β-2,6-fructan (levan), β-1,4-xylan, β-1,3-xylan, β-1,4-chitosan, β-1,4-N-acetyl-chitosan (chitin), pullulan, agarose, arginic acid, cycrodextrins, etc.

Among these, cellulose, amylose, β-1,4-chitosan, β-1,4-acetylchitosan (chitin), β-1,4-mannan, β-1,4-xylan, curdlan, pullulan, dextran, cyclodextrins are preferred for the reason that high purity product is easily obtainable therewith.

The number average degree of polymerization (average number of pyranose rings or franose rings in a molecule) of these polysaccharides excepting cyclodextrins is usually not less than 5, preferably not less than 10. On the other hand, although the ceiling of polymerization degree is not limited, polysaccharides having number average degree of polymerization of not more than 2,000 are easy to handle. Those of not more than 1,000 are more preferred and those of not more than 500 are most preferred.

Preferably usable polysaccharide derivatives are ester derivatives and carbamate derivatives of polysaccharides.

Examples of the especially preferred ester derivatives and carbamate derivatives of polysaccharides are those in which a part of or all of the hydrogen atoms of the hydroxyl or the amino groups of the polysaccharide are substituted with at least one of the groups represented by the following formula (1), (2), (3) or (4):

 (1)

 (2)

 (3)

 (4)

wherein R is an aromatic group which may contain a hetero atom and may be unsubstituted or substituted with at least one group or atom selected from a class consisting of $C_{1-12}$ alkyl group, $C_{1-12}$ alkoxyl group, $C_{1-12}$ alkylthio group, cyano group, halogen atom, $C_{1-8}$ acyl group, $C_{1-8}$ acyloxy group, hydroxyl group, $C_{1-12}$ alkoxycarbonyl group, nitro group, amino group and $C_{1-8}$ dialkylamino group.

Said aromatic hydrocarbyl groups include phenyl group, naphthyl group, phenanthryl group, anthracyl group, indenyl group, indanyl group, furyl group, thionyl group, pyryl group, benzofuryl group, benzothionyl group, indyl group, pyridyl group, pyrimidyl group, quinolyl group, isoquinolyl group, etc. Among these, phenyl, naphthyl, pyridyl, etc. are preferred and alkylphenyl group is most preferred.

In the above formulas, X stands for $C_{1-4}$ hydrocarbyl group, which may contain a double bond or triple bond. Examples thereof are methylene group, methylmethylene group, ethylene group, ethylidene group, ethenylene group, ethynylene group, 1,2- or 1,3-propylene group, 1,2- or 2,2-propylidine group, etc.

The carbamate derivatives of the polysaccharide preferably usable in the present invention are obtained by reacting an isocyanate represented by the following formula (5) or (6) with the polysaccharide, and the ester derivatives of the polysaccharide preferably usable in the present invention are obtained by reacting an acid chloride represented by the following formula (7) or (8) with the polysaccharide:

$$R-N=C=O \quad (5)$$

$$R-X-N=C=O \quad (6)$$

$$R-\underset{\underset{O}{\|}}{C}-Cl \quad (7)$$

$$R-X-\underset{\underset{O}{\|}}{C}-Cl \quad (8)$$

wherein R and X are as defined above.

In the present invention, the degree of introduction of substituent in the polysaccharide is usually 10%–100%, preferably 30%–100% and more preferably 80%–100%. The introduction of less than 10% is not preferable because the polysaccharide has little ability of optical resolution. The introduction of less than 30% is not so preferable because resolution is sometimes insufficient depending upon species and concentration of the optical isomer mixture to be separated. On the other hand, the introduction of in excess of 80% is preferable because particles having excellent optical resolution ability can be obtained. The degree of introduction of substituents can be determined by elemental analysis of carbon, hydrogen and nitrogen before and after the introduction.

In the method of the present invention, said ester derivatives and carbamate derivatives of polysaccharides are used in the form of particles. These particles should preferably be particles of said derivatives per se. The particles may globular or in the crushed form. The method of preparing globular derivatives of polysaccharides is not particularly limited insofar as globular derivatives are obtainable thereby. For instance, a polysaccharide derivative is dissolved in an organic solvent, the solution is dispersed in water which may contain a surfactant, and finally the organic solvent is distilled off by heating or reducing pressure. An example of the method for preparing crushed particles is as follows. A solid lump obtained by dissolving a polysaccharide derivative in an organic solvent and removing the solvent by heating or reducing pressure, or a solid lump obtained by mixing a solution, in which the polysaccharide derivative is dissolved, with a poor soluble solvent, in which solubility of the derivative is extremely low, is crushed by a mill grinder, a freeze crusher, etc.

The obtained particles can be used as is, although they are preferably used after classified into a uniform particle size by a classifier such as air-elutriator, liquid cyclone, blow-shifter, vibration sieve, etc. The classification can also be made by utilizing differences between the particles in sedimentation rate in a slurry.

The employable particle size depends on the size of the used column, etc., and it is usually 10 μm–300 μm, preferably 50 μm–100 μm. It is preferable that the particle size distribution is small. Particle size of less than 10 μm is not preferable because pressure loss in passing of eluent is large. On the other hand, particle size of more than 300 μm is also not preferable because of poor separation caused by reduced number of theoretical plates of the column.

Examples of the eluent usable for the present invention are: hydrocarbons having not less than 5 carbon atoms such as n-hexane, n-pentane, heptane, octane, cyclohexane, isohexane, isooctane, hexene, etc.; alcohols such as methanol, ethanol, n-propanol, isopropanol, butanol, isobutanol, tertiary-butanol, heptanol, hexanol, etc.; water and other organic solvents. They can be used singly or in combination. When used in combination, the solvents must be homogeneously miscible. The eluent may contain acid, base, buffer, salt, etc. A suitable eluent is suitably determined depending upon the species of optical isomer mixture to be separated.

The procedures of separation of optical isomers in the present invention comprises forming a circulatory passage or circuit of a plurality of columns which are packed with the above-described optical resolution filler and connected endlessly; forcing a fluid to circulate through said circuit in one direction; providing the circulatory passage with inlets for introducing a fluid into the columns and outlets for taking a fluid out of the columns alternately and shifting the positions of the inlets and the outlets intermittently in the direction of the flow of the circulating fluid; introducing a mixture of optical isomers and an eluent into the circulatory passage through the inlets and simultaneously taking out a solution rich in non-adsorbable substances and poorly-adsorbable substances and a solution rich in adsorbable or strongly-adsorbable substances through the outlets.

In these procedures, as shown in FIG. 1 for instance, a simulated moving bed comprising a plurality (12 for instance) of unit columns, which are connected in series, is employed in the circulatory passage for circulating a liquid. The liquid is circulated in the liquid passage in one direction. The number of the unit columns in the simulated moving bed is not limited as above-mentioned but optionally selected according to the scale of operation, the viewpoint of reaction engineering, etc.

In the simulated moving bed, an inlet for introducing the eluent; an outlet for taking out the extract, a liquid containing an optical isomer, which is easily adsorbable by the filler; an inlet for introducing the stock solution, i.e., a solution of optical isomer mixture; and an outlet for taking out the raffinate, i.e., a solution containing an optical isomer, which is non-adsorbable or poorly adsorbable by the filler, are provided in this order, and the positions of these inlets and outlets are successively shifted intermittently in the direction of fluid flow.

In the simulated moving bed chromatographic apparatus as shown in FIG. 1, at every third column, an inlet for the eluent, an outlet for the extract, an inlet for the optical isomer mixture solution and an outlet for the raffinate are respectively provided. The positions of these inlets and the outlets are shifted intermittently and successively. For the shifting, a rotary valve, an electromagnetic valve, an air-actuated valve, etc. are employed.

Separation by adsorption of optical isomers in a simulated moving bed chromatographic apparatus is effected by continuously carrying out an adsorption step, a concentration step, a desorption step and an eluent recovery step in circulation.

(1) Adsorption

An optical isomer mixture solution containing not less than two optical isomers are contacted with an optical resolution filler, an optically active isomer easily adsorbable by the filler (adsorbable or strongly adsorbable substance) is adsorbed by the filler while the other optical isomer not easily adsorbable by the filler (non-adsorbable or poorly adsorbable substance) goes into the raffinate, which is recovered together with the eluent.

(2) Concentration

The optical resolution filler, which has adsorbed the adsorbable or strongly adsorbable substance, is contacted with a portion of the extract as described below; non-adsorbable or poorly adsorbable substances remaining in the filler is driven out and the adsorbable or strongly adsorbable substance is concentrated.

(3) Desorption

The optical resolution filler, which contains concentrated adsorbable or strongly adsorbable substance, is contacted with an eluent and the substance is driven out of the optical resolution filler and taken out of the simulated moving bed together with the eluent as the extract.

(4) Recovery of eluent

The optical resolution filler which contains essentially only the eluent is contacted with a portion of the raffinate and a portion of the eluent contained in the optical resolution filler is recovered as an eluent recovery.

Now the procedures are explained in detail with reference to the attached drawing.

In FIG. 1, the members denoted by 1–12 are unit columns packed with an optical resolution filler and they are mutually connected in series by means of conduits. The member 13 is an eluent supply line (conduit). The member 14 is a line (conduit) by which the extract is taken out. The member 15 is a line (conduit) which supplies an optical isomer mixture solution. The member 16 is a line (conduit) by which the raffinate is taken out. The member 17 is a recycle line (conduit). The member 18 is a circulation pump.

In the arrangement of the unit columns 1–12 and the lines (conduits) 13–16 as shown in FIG. 1, desorption, concentration, adsorption and recovery of eluent are respectively effected in columns 1–3, 4–6, 7–8 and 10–12.

In such a simulated moving bed chromatographic apparatus, the eluent supply line (conduit), the line (conduit) for optical isomer mixture solution supply, the line (conduit) for taking out the eluent and the line (conduit) for taking out the raffinate are shifted in the direction of the fluid flow with a constant time interval one column by one column by means of valve operation for instance.

Accordingly, in the second stage, desorption is effected in columns 2–4, concentration is effected in columns 5–7, adsorption is effected in columns 8–10 and eluent recovery is effected in columns 11–1. Such procedure is repeated successively in which each step is effected in a unit column group which is shifted by one column in each stage. Thus, separation of optical isomers is achieved continuously and efficiently.

Figure 2:
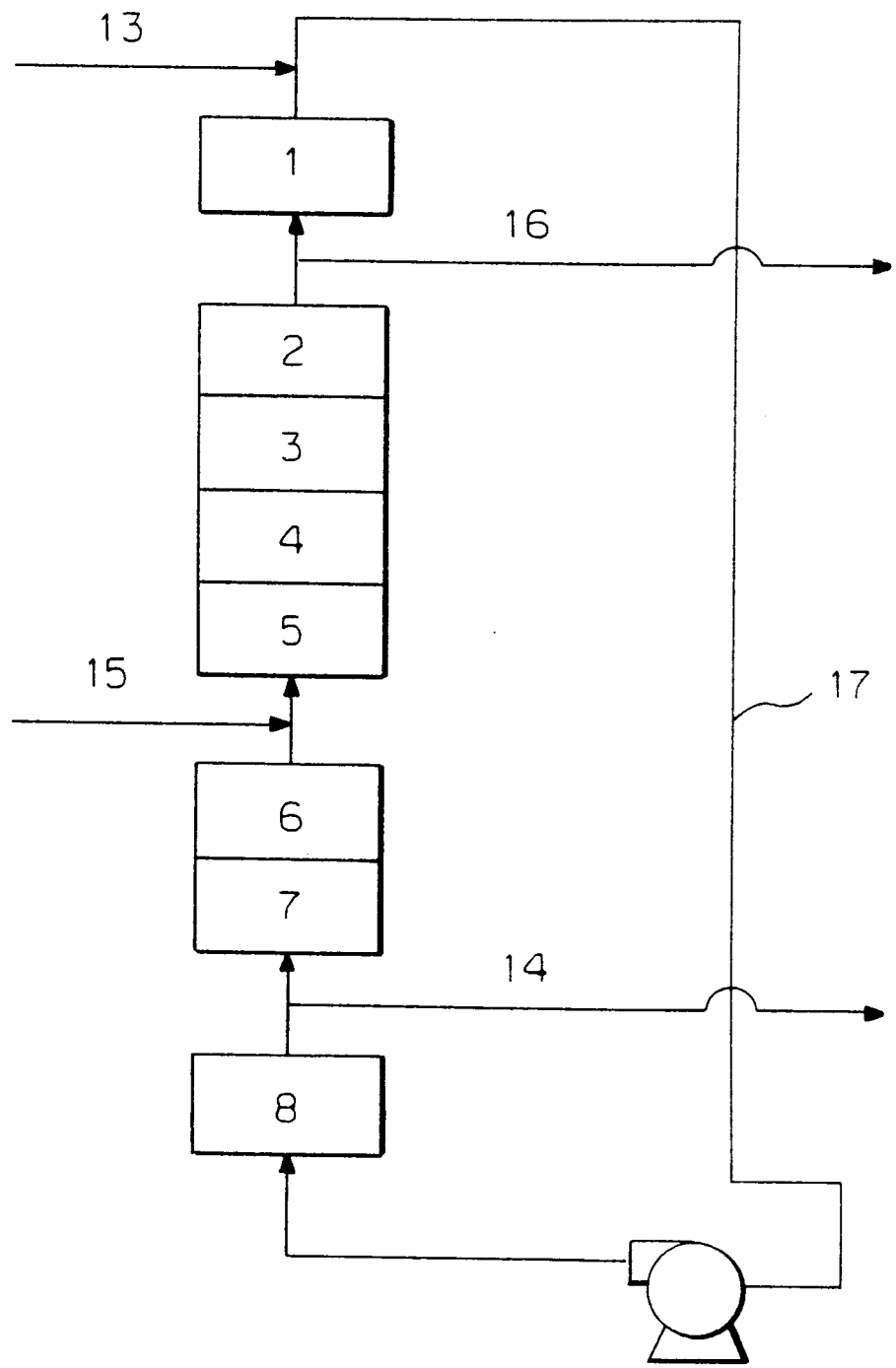
FIG. 2 is a schematic presentation showing another example of the simulated moving bed chromatographic apparatus used for the present invention.

The apparatus usable for the present invention is not limited to the one as represented by FIG. 1, but an apparatus as represented by FIG. 2 is also usable.

With the arrangement of the unit columns 1–8 and lines (conduits) 13–16 as shown in FIG. 2, eluent recovery is effected in unit column 1, adsorption is effected in unit columns 2–5, concentration is effected in unit column 6–7 and desorption is effected in column 8 respectively.

Also in this simulated moving bed, the supply lines (conduits) and the take-out lines (conduits) are shifted by one column in each stage. Thus in the next stage, distribution of the unit columns are as follows. That is, column 2 is for eluent recovery, columns 3–6 are for adsorption, unit columns 7–8 are for concentration and column 1 is for desorption. The stage is repeated and separation of an optical isomer mixture solution is continuously and efficiently achieved.

In FIG. 1, the member 19 is a first falling film evaporator, which concentrates the extract. The member 20 is a second flow down type thin membrane evaporator which further concentrates the concentrated extract. The member 21 is a wiped film evaporator which still further concentrates the concentrated extract. The member 22 is a recovery tank which temporarily stores a recovered solvent. The member 23 is a storage tank for storing the optical isomer concentrate which has been concentrated by the evaporators. The member 24 is a racemization reactor in which an optical isomer mixture is racemized. The member 25 is a distillator, in which the solvent stored in the recovery tank 22, is purified to a desired degree.

The raffinate contains another optical isomer which is an antipode of the optical isomer contained in the extract and the solvent. The solvent can be recovered by the same way as recovery of the solvent from the extract.

Now the invention will be described by way of working examples. Needless to say, the invention is not limited to these specific examples but can be carried out in various modified modes within the gist of the invention.

EXAMPLE 1

Preparation of globular particles of cellulose tris(3, 5-dimethylphenylcarbamate)

Five hundred grams (500 g) of cellulose tris(3,5-dimethylphenylcarbamate) was dissolved in a mixed solution of 12.5 liters of mesityl oxide and 2.5 liters of acetone and 2.5 liters of n-nonane was added. The solution was poured into 30 liters of a 0.75% aqueous solution of sodium lauryl sulfate, which was being stirred by 100 rpm rotation and well mixed. The solution was heated to 40° C. while stirring and the organic solvent was distilled off by reducing pressure. After filtration, the isolated residue was washed with water and ethanol and vacuum-dried at 140° C. for 24 hours. Thus 462 g of powder was obtained. The yield was 92.4%. The obtained powder was sieved and particles having an average particle diameter of 52 $\mu$m were collected. The specific surface area of the particles was 4.3 m$^2$/g (by BET method).

EXAMPLE 2

Preparation of crushed particles of cellulose tris(3, 5-dimethylphenylcarbamate)

Five hundred grams (500 g) of cellulose tris(3,5-dimethylphenylcarbamate) was dissolved in 3 liters of acetone. The solution was poured into 30 liters of methanol, which was being stirred by 100 rpm rotation, through a nozzle, and the product was solidified. The formed precipitate was isolated by filtration and vaccum-dried at 140° C. for 24 hours. The collected product weighed 476 g and the yield was 95.2%. The solid product was crushed with a crusher. After crushing, the particles were sieved and the crushed particles having an average particle diameter of 46 $\mu$m were obtained. The specific surface area was 3.5 m$^2$/g (by BET method).

EXAMPLE 3

Preparation of globular particles of cellulose tri(p-methylbenzoate)

Five hundred grams (500 g) of cellulose tri(p-methylbenzoate) was dissolved in 15 liters of methylene chloride, 2.5 liters of n-nonane was added to the solution and well mixed. The resulting solution was poured into 30 liters of a 0.75% aqueous solution of sodium lauryl sulfate under stirring by 100 rpm rotation and well mixed. The resulting solution was heated to 45° C. under stirring as previous and thus methylene chloride was distilled off. The residue isolated by filtration was washed with water and methanol and vacuum-dried at 140° C. for 24 hours. Thus 432 g of a powder was obtained. The yield was 86.4%. The obtained particles were sieved and the particles having an average particle diameter of 47 μm was collected. The specific surface area of these particles was 5.2 m$^2$/g (by BET method).

EXAMPLE 4

Separation of propranolol with polysaccharide derivative particles obtained in Example 1 as optical resolution filler In a simulated moving bed chromatographic apparatus comprising 8 preparative columns having an inside diameter of 1 cm and a length of 25 cm, which was packed with globular particles of cellulose tris(3,5-dimethylphenyl-carbamate) obtained in Example 1, racemic propranolol was supplied at a rate of 0.3 ml/min. (The racemic compound concentration was 26.6 mg/ml.)

The operation conditions of the simulated moving bed chromatographic apparatus were as follows:

Eluent: a mixture of n-hexane and 2-propanol n-hexane/2-propanol volume ratio =8/2

Supply rate of eluent: 2.9 ml/min.

Take-out flow rate of the fluid rich in adsorbable or strongly adsorbable substance: 2.5 ml/min.

Take-out flow rate of the fluid rich in non-adsorbable or poorly adsorbable substances: 0.7 ml/min.

Flow rate of recovered eluent: 0.3 ml/min.

Column shift time interval: 30.5 min.

Temp.: 25° C.

Optical resolution was carried out under the above-described conditions. At the outlet for the fluid containing adsorbable or strongly adsorbable substance, a solution containing 2350 ppm of (−)-propranolol having optical purity of 95% ee. was taken out. At the outlet for the fluid containing non adsorbable or poorly adsorbable substances, a solution containing 8290 ppm of (+)-propranolol having an optical purity of 100% ee was taken out.

EXAMPLE 5

Separation of methyl-2-phenoxy propionate with polysaccharide derivative particles obtained in Example 3 as optical resolution filler In a simulated moving bed chromatographic apparatus comprising 8 preparative columns having an inside diameter of 1 cm and a length of 25 cm packed with globular particles of cellulose tri(p-methylbenzoate) obtained in Example 3, racemic methyl 2-phenoxypropionate was supplied at a rate of 0.1 ml/min. (The racemic compound concentration was 10 mg/ml.)

The operation conditions of the simulated moving bed chromatographic apparatus were as follows:

Eluent: a mixture of n-hexane and 2-propanol n-hexane/2-propanol volume ratio =9/1

Supply rate of eluent: 3 ml/min.

Take-out flow rate of the fluid rich in adsorbable or strongly adsorbable substance: 1.5 ml/min.

Take-out flow rate of the fluid rich in non-adsorbable or poorly adsorbable substances: 1.6 ml/min.

Flow rate of recovered eluent: 0.1 ml/min.

Column shift time interval: 15.5 min.

Temp.: 25° C.

Optical resolution was carried out under the above-described conditions. At the outlet for fluid containing adsorbable or strongly adsorbable substance, a solution containing 506 ppm of (−)-methyl 2-phenoxypropionate having an optical purity of 96% ee. was taken out. At the outlet for fluid containing non adsorbable or poorly adsorbable substances, a solution containing 460 ppm of (+)-methyl-2-phenoxypropionate having an optical purity of 100% ee was taken out.

INDUSTRIAL APPLICABILITY

The present invention provides a method for separation of optical isomers not using expensive silica gel but using a adsorbent, which is inexpensive per se and has excellent optical resolution ability, as a optical resolution filler.

The present invention enables efficient and economical production of a desired optical isomer with high optical purity by optical resolution of a racemic compound or a mixture which is obtained by asymmetric synthesis and contains one optical isomer in excess.

The present invention provides a method for optical resolution which not only achieves efficient separation but also consumes far less amount of eluent.

What is claimed is:

1. A method of separation of optical isomers using a simulated moving bed chromatographic apparatus which comprises:

forming a circulation circuit comprising a plurality of columns each provided with an inlet port and an outlet port and packed with particles of polysaccharide derivatives, said columns being serially and endlessly connected so as to achieve serial and unidirectional fluid flow through said columns, wherein the particles of polysaccharide derivatives are not supported on a silica gel carrier;

introducing an optical isomer mixture to be separated into one of the columns via the inlet port thereof in order to cause adsorbable or strongly adsorbable substances to become adsorbed on the particles of polysaccharide derivatives in the column and several columns that follow;

drawing out a solution rich in the other substances being non-adsorbable or poorly adsorbable on the particles of polysaccharide derivatives via the outlet port of another one of the columns;

introducing an eluent into still another one of the columns via the inlet port thereof;

drawing out a solution rich in the adsorbable or strongly adsorbable substances via the outlet port of further another one of the columns; and passing the remaining solution and the eluent through the circuit and recirculating them, wherein the position for introducing the eluent, the position for drawing out the solution containing the adsorbable or strongly adsorbable substances, the position for introducing the optical isomer mixture and the position for drawing out the solution containing the non-adsorbable or weakly adsorbable substances are arranged in the circulation in this order along the direction of the fluid flow, and the positions are successively moved in the direction of the fluid flow in the circuit intermittently.

2. A method of separation of optical isomers as defined in claim 1, wherein the polysaccharide derivatives are ester derivatives or carbamate derivatives of polysaccharides.

3. A method of separation of optical isomers as defined in claim 1, wherein the polysaccharide derivatives are polysaccharides in which part of or all of the hydrogen atoms on the hydroxyl or amino groups are substituted with one of the groups represented by the formula (1), (2), (3) or (4):

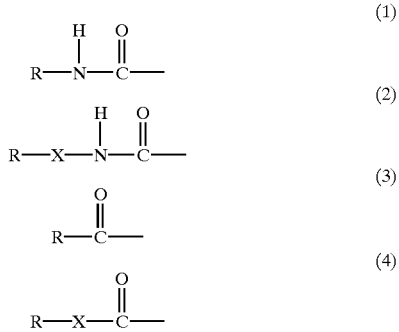

wherein R is an aromatic group which may contain a hetero atom and may be unsubstituted or substituted with at least one group or atom selected from the class consisting of $C_{1-12}$ alkyl group, $C_{1-12}$ alkoxyl group, $C_{1-12}$ alkylthio group, cyano group, halogen atom, $C_{1-8}$ acyl group, $C_{1-8}$ acyloxy group, hydroxyl group, $C_{1-12}$ alkoxycarbonyl group, nitro group, amino group and $C_{1-8}$ dialkylamino group and X stands for $C_{1-4}$ hydrocarbyl group, which may contain a double bond or triple bond.

4. A method of separation of optical isomers as defined in claim 1, wherein the polysaccharide derivatives are polysaccharide carbamate derivatives obtained by reacting an isocyanate represented by the following formula (5) or (6) with a polysaccharide, or polysaccharide ester derivatives obtained by reacting an acid chloride represented by the following formula (7) or (8) with a polysaccharide:

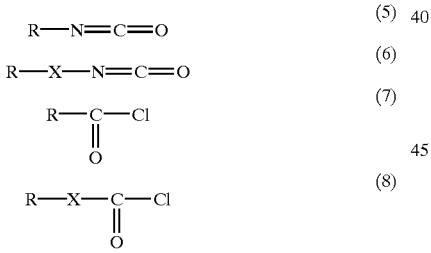

wherein R is an aromatic group which may contain a hetero atom and may be unsubstituted or substituted with at least one group or atom selected from the class consisting of $C_{1-12}$ alkyl group, $C_{1-12}$ alkoxyl group, $C_{1-12}$ alkylthio group, cyano group, halogen atom, $C_{1-8}$ acyl group, $C_{1-8}$ acyloxy group, hydroxyl group, $C_{1-12}$ alkoxycarbonyl group, nitro group, amino group and $C_{1-8}$ dialkylamino group and X stands for $C_{1-4}$ hydrocarbyl group, which may contain a double bond or triple bond.

5. A method of separation of optical isomers as defined in claim 1, wherein the polysaccharide is cellulose.

6. A method of separation of optical isomers as defined in claim 1, wherein the polysaccharide has a number average degree of polymerization of not less than 5.

7. A method of separation of optical isomers as defined in claim 1, wherein the polysaccharide has an average degree of polymerization of 10 to 2,000.

8. A method of separation of optical isomers as defined in claim 1, wherein the degree of introduction of the substituent of the polysaccharide derivatives is 10 to 100%.

9. A method of separation of optical isomers as defined in claim 1, wherein the degree of introduction of the substituent of the polysaccharide derivatives is 30 to 100%.

10. A method of separation of optical isomers as defined in claim 1, wherein the polysaccharide derivative has an average particle diameter of 10 to 300 $\mu$m and a specific surface area of 0.5 to 300 $m^2/g$.

11. In a method of separation of optical isomers using a simulated moving bed chromatographic apparatus which comprises:

forming a circulation circuit comprising a plurality of columns each provided with an inlet port and an outlet port and packed with an optical resolution filler, said columns being serially and endlessly connected so as to achieve serial and unidirectional fluid flow through said columns;

introducing an optical isomer mixture to be separated into one of the columns via the inlet port thereof in order to cause adsorbable or strongly adsorbable substances to become adsorbed on the optical resolution filler in the column and several columns that follow;

drawing out a solution rich in the other substances being non-adsorbable or poorly adsorbable on the optical resolution filler via the outlet port of another one of the columns;

introducing an eluent into still another one of the columns via the inlet port thereof;

drawing out a solution rich in the adsorbable or strongly adsorbable substances via the outlet port of further another one of the columns; and passing the remaining solution and the eluent through the circuit and recirculating them, wherein the position for introducing the eluent, the position for drawing out the solution containing the adsorbable or strongly adsorbable substances, the position for introducing the optical isomer mixture and the position for drawing out the solution containing the non-adsorbable or weakly adsorbable substances are arranged in the circulation in this order along the direction of the fluid flow, and the positions are successively moved in the direction of the fluid flow in the circuit intermittently, the improvement which comprises using particles of polysaccharide derivatives as the optical resolution filler, wherein the particles of polysaccharide derivatives are not supported on a silica gel carrier.

* * * * *